(12) United States Patent
Ganga et al.

(10) Patent No.: US 11,066,439 B2
(45) Date of Patent: Jul. 20, 2021

(54) SYNTHESIS OF LIRAGLUTIDE

(71) Applicant: Biocon Limited, Bangalore (IN)

(72) Inventors: Ramu Vasanthakumar Ganga, Bengaluru (IN); Nitin Patil, Bangalore (IN); Palle Venkata Raghavendra Charyulu, Hyderabad (IN); Castelino Roopa Jasmine, Bengaluru (IN); Rambabu Machani, Kurnool (IN); Deepa Shankar Suvarna, Bengaluru (IN)

(73) Assignee: Biocon Limited, Electronic (IN)

( * ) Notice: Subject to any disclaimer, the term of this patent is extended or adjusted under 35 U.S.C. 154(b) by 0 days.

(21) Appl. No.: 16/468,190

(22) PCT Filed: Dec. 9, 2017

(86) PCT No.: PCT/IB2017/057763
§ 371 (c)(1),
(2) Date: Jun. 10, 2019

(87) PCT Pub. No.: WO2018/104922
PCT Pub. Date: Jun. 14, 2018

(65) Prior Publication Data
US 2020/0079817 A1    Mar. 12, 2020

(30) Foreign Application Priority Data
Dec. 10, 2016 (IN) .............................. 201641042252

(51) Int. Cl.
| C07K 1/10 | (2006.01) |
| C07K 1/02 | (2006.01) |
| C07K 14/00 | (2006.01) |
| C07K 14/605 | (2006.01) |

(52) U.S. Cl.
CPC .................. *C07K 1/10* (2013.01); *C07K 1/02* (2013.01); *C07K 14/001* (2013.01); *C07K 14/605* (2013.01)

(58) Field of Classification Search
CPC .......... C07K 1/10; C07K 1/02; C07K 14/001; C07K 14/605; A61P 3/10; A61K 47/542; Y02P 20/55
See application file for complete search history.

(56) References Cited

U.S. PATENT DOCUMENTS

| 6,268,343 B1 | 7/2001 | Knudsen et al. |
| 6,451,974 B1 | 9/2002 | Hansen |
| 7,273,921 B2 | 9/2007 | Dunweber et al. |
| 9,260,474 B2 | 2/2016 | Pan et al. |

FOREIGN PATENT DOCUMENTS

| WO | 2014/199397 A2 | 12/2014 |
| WO | 2016/059609 A1 | 4/2016 |

OTHER PUBLICATIONS

Thaler et al (Helvetica Chimica Acta, 1991, 74, 628-643). (Year: 1991).*
Ryadnov et al (J.Peptide Res., 1999, 53, 322-328) (Year: 1999).*
Miyazawa et al (Int.J.Peptide Protein Res., 1992, 39, 237-244). (Year: 1992).*
Li et al (Organic Letters, 1999, vol. 1, No. 1, 91-93) (Year: 1999).*
Bourel et al (Journal of Peptide Science, 2000, 6, 264-270) (Year: 2000).*
Yano et al (Biochemical and Biophysical Research Communications, 2008, 371, 846-849) (Year: 2008).*
Futaki et al (JACS, 2004, 126, 15762-15769) (Year: 2004).*
International Search Report for International Application No. PCT/IB/057763 dated Mar. 14, 2018.

\* cited by examiner

*Primary Examiner* — Sudhakar Katakam
(74) *Attorney, Agent, or Firm* — Katten Muchin Rosenman LLP

(57) ABSTRACT

The present invention relates to the efficient solid-phase synthesis of liraglutide represented by Formula-I. The present invention relates to an efficient process for the preparation of liraglutide by sequential coupling employing solid phase approach. It involves sequential coupling of protected amino acids to prepare backbone of liraglutide and upon completion of linear sequence, synthesis was extended from lysine side chain by adding γ-glutamic acid and palmitic acid, followed by removal of protective groups, cleavage of the peptide from solid support and purification of crude liraglutide obtained. The present invention also involves the usage of inorganic salts during the coupling, wash with HOBt in DMF solution after Fmoc-deprotection step to suppress the aggregation of peptides and ensure reactions are going for completion, and thus avoid deletion sequences and improve the process yield.

14 Claims, 3 Drawing Sheets

Figure – 1A

Boc–His(Trt)$^7$–Ala$^8$–Glu(OtBu)$^9$–Gly$^{10}$–Thr(tBu)$^{11}$–Phe$^{12}$–Thr(tBu)$^{13}$–Ser(tBu)$^{14}$–Asp(OtBu)$^{15}$–Val$^{16}$– Ser(tBu)$^{17}$ –Ser(tBu)$^{18}$–Tyr(tBu)$^{19}$–Leu$^{20}$–Glu(OtBu)$^{21}$–Gly$^{22}$–Gln(Trt)$^{23}$–Ala$^{24}$-Ala$^{25}$–Lys(Fmoc-Glu-OtBu)$^{26}$–Glu(OtBu)$^{27}$–Phe$^{28}$–Ile$^{29}$–Ala$^{30}$–Trp(Boc)$^{31}$–Leu$^{32}$–Val$^{33}$–Arg(Pbf)$^{34}$–Gly$^{35}$-Arg(Pbf)$^{36}$–Gly$^{37}$–Wang Resin 9. Deprotection of Fmoc with 15 - 25 % piperidine/DMF
10. Coupling of hexadecanoic acid using DEPBT, COMU, DIC, HBTU/HOBt, Oxymapure Boc–His(Trt)$^7$–Ala$^8$–Glu(OtBu)$^9$–Gly$^{10}$–Thr(tBu)$^{11}$–Phe$^{12}$–Thr(tBu)$^{13}$–Ser(tBu)$^{14}$–Asp(OtBu)$^{15}$–Val$^{16}$– Ser(tBu)$^{17}$ –Ser(tBu)$^{18}$–Tyr(tBu)$^{19}$–Leu$^{20}$–Glu(OtBu)$^{21}$–Gly$^{22}$–Gln(Trt)$^{23}$–Ala$^{24}$-Ala$^{25}$–Lys(Palmitoyl-Glu-OtBu)$^{26}$–Glu(OtBu)$^{27}$–Phe$^{28}$–Ile$^{29}$–Ala$^{30}$–Trp(Boc)$^{31}$–Leu$^{32}$–Val$^{33}$–Arg(Pbf)$^{34}$–Gly$^{35}$-Arg(Pbf)$^{36}$–Gly$^{37}$–Wang Resin 11. Release of peptide from resin and total cleavage with 80% TFA cocktail containing scavengers H–His$^7$–Ala$^8$–Glu$^9$–Gly$^{10}$–Thr$^{11}$–Phe$^{12}$–Thr$^{13}$–Ser$^{14}$–Asp$^{15}$–Val$^{16}$– Ser$^{17}$ –Ser$^{18}$–Tyr$^{19}$–Leu$^{20}$–Glu$^{21}$–Gly$^{22}$–Gln$^{23}$–Ala$^{24}$-Ala$^{25}$–Lys(γ-Glu-palmitoyl)$^{26}$–Glu$^{27}$–Phe$^{28}$–Ile$^{29}$–Ala$^{30}$–Trp$^{31}$–Leu$^{32}$–Val$^{33}$–Arg$^{34}$–Gly$^{35}$-Arg$^{36}$–Gly$^{37}$– OH Crude Liraglutide

SYNTHESIS OF LIRAGLUTIDE

TECHNICAL FIELD OF THE INVENTION

The present invention relates to the efficient solid-phase synthesis of liraglutide represented by Formula-I.

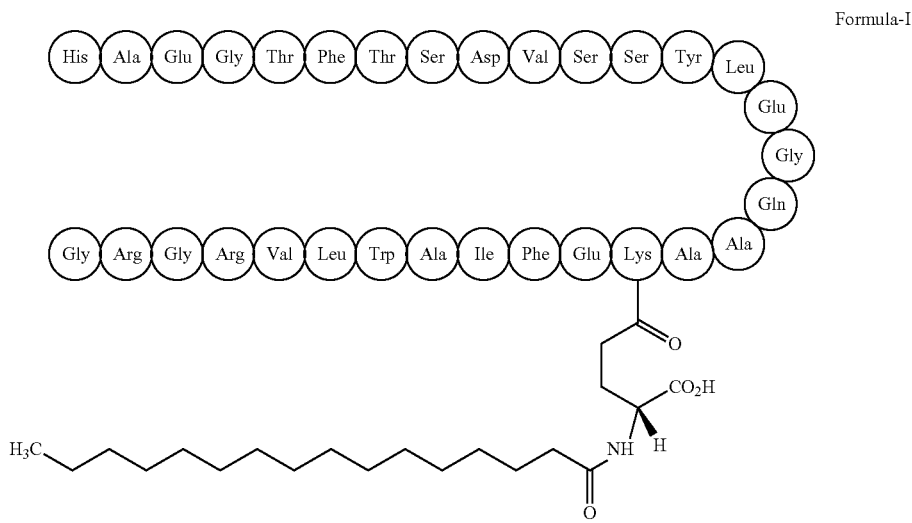 [SMILES: CCCCCCCCCCCCCCCC(=O)N[C@H](CCC(C)=O)C(=O)O]

Formula-I

Liraglutide (VICTOZA®) is a glucagon-like peptide-1 (GLP-1) receptor agonist indicated as an adjunct to diet and exercise to improve glycemic control in adults with type 2 diabetes mellitus.

BACKGROUND OF THE INVENTION

Liraglutide, is a long acting analogue of the naturally occurring human glucagon like peptide-1 (GLP-1(7-37)) in which lysine at position 34 has been replaced with arginine and palmitoyl group has been attached via glutamoyl spacer to lysine at position 26.

Liraglutide (VICTOZA®), developed by Novo Nordisk got initial approval in United States in 2010 as subcutaneous injection.

U.S. Pat. No. 6,268,343 discloses liraglutide and process for preparing it. Wherein recombinant technology is involved in preparing $Arg^{34}$-GLP-1(7-37)-OH followed by reaction with $N^{\alpha}$-hexadecanoyl-Glu(ONSu)—$O^{t}Bu$.

U.S. Pat. Nos. 7,273,921 B2 and 6,451,974 B1 discloses process for acylation of $Arg^{34}$-GLP-1(7-37)-OH to obtain liraglutide.

U.S. 9,260,474 B2 discloses solid phase synthesis of liraglutide characterised in that comprises a) sequential coupling of amino acids with ti-terminal protection and side chain protection based on the sequence of peptide backbone of liraglutide, wherein Fmoc-Lys(Alloc)-OH is employed for lysine;
b) deprotection of Alloc on the side chain of lysine;
c) coupling of palmitoyl-Glu-OtBu or sequential coupling of glutamic acid and palmitoyl chloride to the side chain of lysine;
d) removal of protective groups and cleavage of resin to obtain crude liraglutide.

WO 2014/199397 A2 discloses solid phase synthesis of liraglutide using sequential coupling approach and fragment approach, wherein Fmoc-Lys(dde)-OH is employed for lysine.

WO 2016/059609 A1 discloses process for acyl $Arg^{34}$-GLP-1(7-37)-OH using copper agent to obtain liraglutide.

The prior processes for preparing liraglutide have disadvantages. The methods are not suitable for large scale production of liraglutide due to complex techniques and high costs; in processes where Alloc is employed as lysine side chain protecting group, deprotection of Allot requires metal catalysts such as $Pd(PPh_3)_4$ which are rather expensive. Further, catalyst is moisture sensitive, reaction has to be carried out in controlled conditions and heavy metal content in final product to be considered. Hence, the processes are not commercially viable or execution problems persist.

During solid phase synthesis, it is observed that sturdy tendency of peptides to aggregate under conditions employed. It is because of the following reasons:
a) Growing peptide sequence is susceptible to form β-sheet kind of structures, which results in collapse of the peptidyl resin and
b) Hydrophobic amino acids present which cause folded peptide chain.

In such conditions, the dispersion of reagents into the peptidyl resin is limited, coupling and deprotection reactions will be sluggish and incomplete, thereby generating peptide impurities leading to difficulties in purification and resulting in low yield. Hence, there remains a need to provide efficient process for preparation of liraglutide which is high yielding, scalable, cost effective, environment friendly and commercially viable by avoiding repeated cumbersome and lengthy purification steps.

OBJECTS OF THE INVENTION

The objective of the present invention is to develop simple, robust, and commercially viable sequential process for the preparation of liraglutide of the Formula 1 with the aid of inorganic salts, novel and efficient coupling conditions.

BRIEF DESCRIPTION OF DRAWINGS

FIG. 1A: Flow chart for process for solid-phase synthesis of liraglutide (Formula-I) showing steps 9-11 according to the present invention.

SUMMARY OF THE INVENTION

An embodiment of the present invention involves synthetic process for the preparation of liraglutide comprising the following steps:
- a) Loading of C-terminal glycine to a resin solid-phase support in the presence of coupling agent.
- b) Sequential coupling of Nα- and side chain protected amino acids to prepare backbone of liraglutide, in the presence of coupling agent and an inorganic salt.
- c) Deprotection of side chain protecting group of lysine.
- d) Coupling of γ-glutamic acid and palmitic acid in sequential manner to the side chain of lysine in the presence of coupling agent and an inorganic salt.
- e) Crude liraglutide is obtained by removal of protective groups and cleavage of peptide from the resin.
- f) Purification of crude liraglutide.

Figure 1:
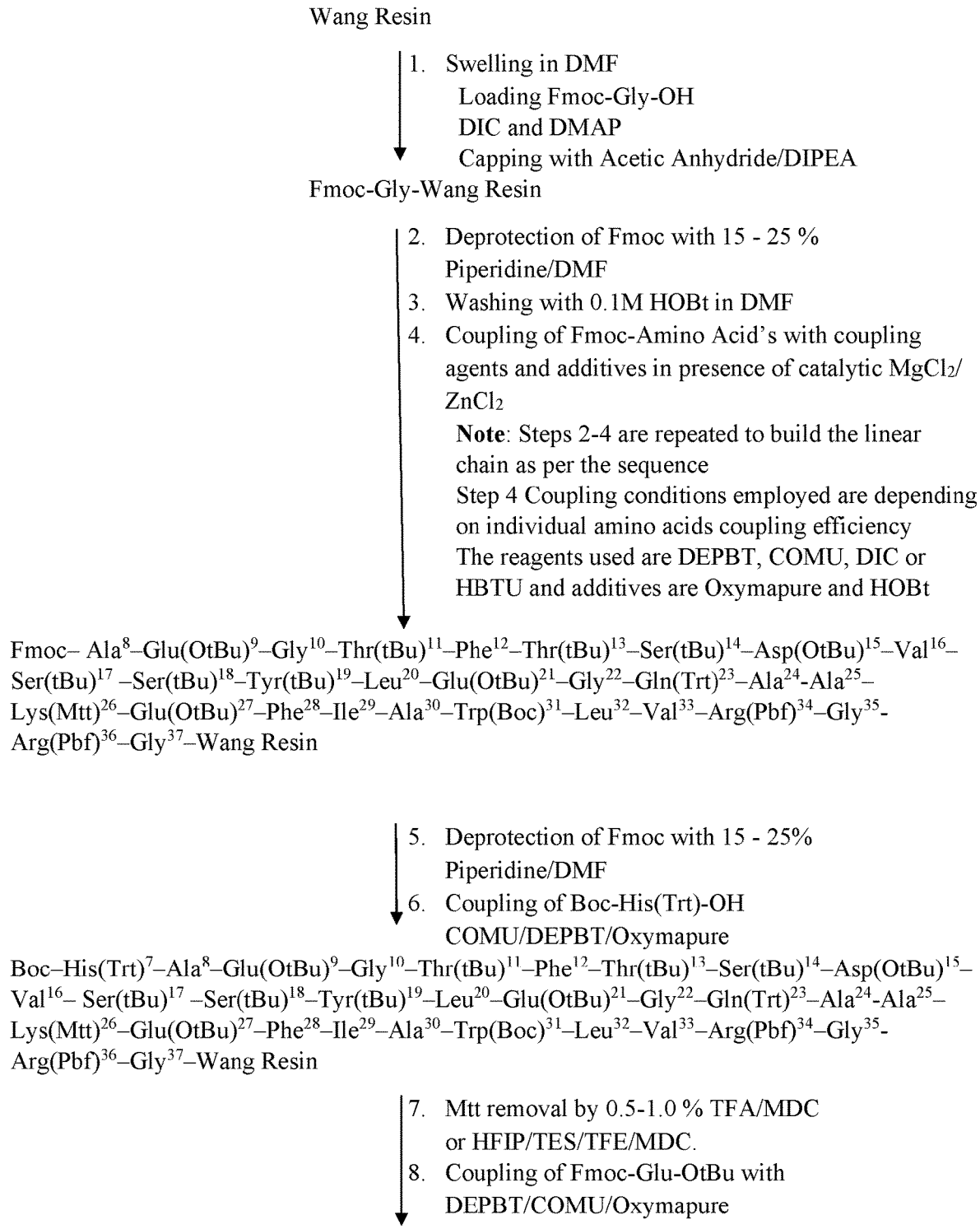
FIG. 1: Flow chart for process for solid-phase synthesis of liraglutide (Formula-I) showing steps 1-8 according to the present invention.
Figure 2:
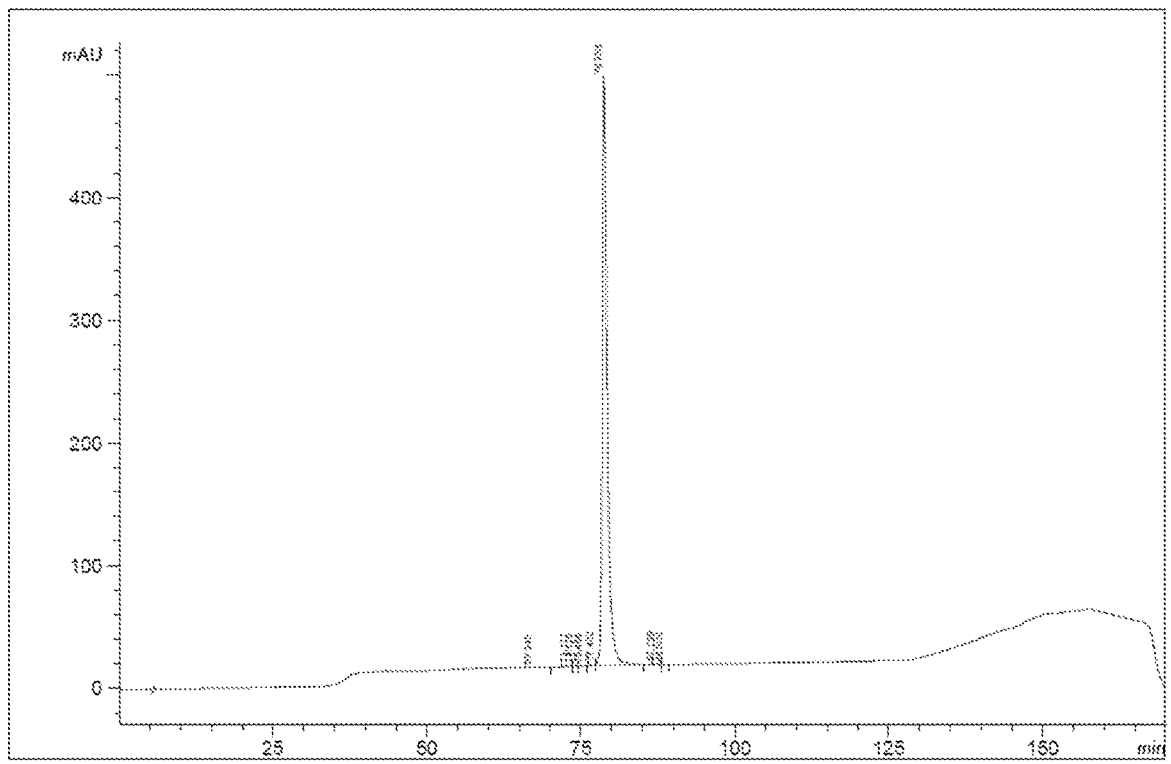
FIG. 2: Illustrates HPLC chromatogram of Liraglutide

The schematic description of the process is as shown in FIG. 1 and FIG. 1A.

The approach employed is solid phase peptide synthesis of liraglutide by sequential approach and involves inorganic salts during coupling along with regular coupling agents and additives. The method offers completion of coupling and deprotection reactions and reduction in racemization and thereby control the isomeric impurities which are very close to the target molecule and in turn ease the purification process of the peptide.

For further improving the present invention, in said step-A). wang resin is employed as resin solid-phase support and coupled to Fmoc-Gly-OH using, DIC as coupling agent and MDC as solvent.

The use of 2-chlorotrityl resin (CTC) as solid-phase support was limited because couplings were sluggish and not going for completion after 15 amino acids sequence and the peptide attached to CTC resin being labile and prone to be leached out in mild acidic conditions employed during coupling/washing cycles. Since, synthesis of liraglutide involves multistep, at each stage partial leaching occurs leading to reduction in overall yield.

For further improving of the present invention, in said step-B), comprises following steps:
B1) deprotection of Fmoc protecting group from Fmoc-Gly-resin using Piperidine/DMF or Piperidine, DBU, DMF mixture to get H-Gly-resin.
B2) washing the loaded resin
B3) coupling of Fmoc-Arg(Pbf)-OH to H-Gly-resin in the presence of coupling agent, coupling additive, inorganic salt and base.
B4) by repeating steps B1, B2 and B3, liraglutide backbone is synthesized, wherein in step-B3 protected amino acids are sequentially coupled to get liraglutide backbone.

For Further improving the present invention, in said step-B) and D) coupling agent was selected from the group consisting of HBTU, COMU, DEPBT or DIC.

Coupling additive was selected from the group consisting of oxyma pure or HOBt, base was selected from DIPEA, NMM or TMP and inorganic salt selected from the group consisting of magnesium chloride, zinc chloride or copper chloride.

As said in step-B2) loaded resin was washed with 0.01-0.1 M HOBt in DMF or Isopropanol For further improving the present invention, as said in step-B), Mtt used as protective group for lysine and as said in step-C), the protective group Mtt from the side chain of lysine removed by using TFA/MDC or HFIP/TES/TFE/MDC.

For Further improving the present invention, in said step-D), palmitoyl-glutamic acid (Pal-Glu) side chain coupled in the presence of coupling agent selected from the group consisting or HBTU, COMU, DEPBT or DIC; coupling additive selected from the group consisting of oxyma pure or HOBt; base selected from DIPEA, NMM or TMP and inorganic salt selected from the group consisting of magnesium chloride, zinc chloride or copper chloride.

Another embodiment of the present invention involves synthetic process for the preparation of liraglutide comprising the following steps:
- a) Coupling of Nα-Fmoc-protected glycine (Fmoc-Gly-OH) to a resin solid-phase support in the presence of coupling agent,
- b) Sequential coupling of Nα- and side chain protected amino acids to prepare backbone of liraglutide, in the presence of coupling agent and an inorganic salt,
- c) Deprotection of side chain protecting group of lysine.
- d) Coupling of palmitoyl-glutamic acid (Pal-Glu) side chain to the side chain of lysine in the presence of coupling agent and an inorganic salt.)
- e) Crude liraglutide is obtained by removal of protective groups and cleavage of peptide from the resin.
- f) Purification of crude liraglutide.

For Further improving the present invention, in said step-D), palmitoyl-glutamic acid (Pal-Glu) side chain coupled in the presence of coupling agent selected from the group consisting of HBTU, COMU, DEPBT or DIC; coupling additive selected from the group consisting of oxyma pure or HOBt; base selected from DIPEA, NMM or TMP and inorganic salt selected from the group consisting of magnesium chloride, zinc chloride or copper chloride.

Yet another embodiment of the present invention involves synthetic process for the preparation of liraglutide comprising the following steps:
- i) Coupling of Nα-Fmoc-protected glycine (Fmoc-Gly-OH) to a resin solid-phase support in the presence of coupling agent.
- ii) Sequential coupling of Nα- and side chain protected amino acids to prepare backbone of liraglutide, in the presence of coupling agent and an inorganic salt.
- iii) Fmoc-deprotection of the loaded amino acid using piperidine in DMF or Piperidine/DBU/DMF mixture,
- iv) After each Fmoc de protection step washing step using HOBt in DMF.
- v) Deprotection of side chain protecting group of lysine
- vi) Coupling of palmitoyl-glutamic acid (Pal-Glu) side chain to the side chain of lysine in the presence of coupling agent and an inorganic salt.
- vii) Crude liraglutide is obtained by removal of protective groups and cleavage of peptide from the resin. Purification of crude liraglutide.

Further as an improvements to the above embodiments, amino acids numbered 9 to 13 [i.e Fmoc-Glu(OtBu)$^9$, Fmoc-Gly$^{10}$, Fmoc-Thr(tBu)$^{11}$, Fmoc-Phe$^{12}$, Fmoc-Thr(tBu)$^{13}$] are coupled at an elevated temperature of around 30-45° C. to form liraglutide backbone.

DETAILED DESCRIPTION OF THE INVENTION

The present invention relates to an efficient process for the preparation of liraglutide by sequential coupling employing solid phase approach. It involves sequential coupling of protected amino acids to prepare backbone of liraglutide and upon completion of linear sequence, synthesis was extended from lysine side chain by adding γ-glutamic acid and palmitic acid, followed by removal of protective groups, cleavage of the peptide from solid support and purification of crude liraglutide obtained. The present invention also involves the usage of inorganic salts during the coupling, wash with HOBt in DMF solution after Fmoc-deprotection step to suppress the aggregation of peptides and ensure reactions are going for completion, and thus avoid deletion sequences and improve the process yield.

ABBREVIATIONS

ACN: Acetonitrile
Boc: tert-Butyloxycarbonyl
COMU: 1-Cyano-2-ethoxy-2-oxoethylidenaminooxy)dimethylamino-morpholino-carbenium hexafluorophosphate
$CuCl_2$: Copper chloride
DBU: 1,8-Diazabicyclo[5.4.0]undec-7-ene
DEPBT: 3-(Diethoxyphosphoryloxy)-1,2,3-benzotriazin-4(3H)-one
DIC: N,N'-diisopropylcarbodiimide
DMAP: Dimethylamino pyridine
DMF: N,N'-Dimethylformamide
DIPEA: Diisopropylethylamine
Fmoc: 9-fluorenylmethoxycarbonyl
HBTU: O-Benzotriazole-N,N,N'N'-tetramethyl uronium hexafluorophosphate
HOBt: N-Hydroxybenzotriazole
HFIP: 1,1,1,3,3,3-Hexafluro-2-propanol
Mtt: Methyltrityl
MeOH: Methanol
$MgCl_2$: Magnesium Chloride
NNM: N-methylmorpholine
NMP: N-Methyl-2-pyrrolidone
TES: Triethylsilane
TFE: Trifluroethanol
TPA: Trifluoroacetic acid
Pbf: 2,2,4,6,7-Pentamethyldihydrobenzofurane
$Pd(PPh_3)_4$: Tetrakis)triphenylphosphine)palladium(0)
RT: Room temperature
$^tBu$: tert-Butyl
TIS: Triisopropyl Silane
Trt: Trityl
TMP: 2,4,6-Trimethylpyridine
$ZnCl_2$: Zinc chloride The invention is represented by following examples. These examples are for illustration only and hence should not be construed as limitation of the scope of invention.

EXAMPLE 1

Synthesis of Liraglutide Using $MgCl_2$

Stage-1 Synthesis of Fmoc-Gly$^{37}$-Wang Resin

The Wang, resin (0.3-0.6 mmol/g, loading capacity) was loaded to peptide synthesis vessel, washed twice with 10 v of MDC, decanted the washings, added 10 v of MDC and kept for swelling for 1 h. Fmoc-Gly-OH (3.0-5.0 eq.) was dissolved in MDC, added minimum quantity of DMF to obtain clear solution and the mixture was transferred to reaction vessel. Added DIPC (3.0-6.0 eq.) followed by DMAP (0.01-0.1 eq.) to the reaction vessel and stirred for 1.0-3.0 h, at rt. Drained the reaction mass and washed the amino acid loaded resin twice with MDC followed by DMF. Capping of the unreacted functional sites were carried out using acetic anhydride and DIPEA.

Stage-2: Synthesis of Fmoc-Arg(Pbf)$^{36}$-Gly$^{37}$-Wang Resin

Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Arg(Pbf)-OH (2.0-4.0 eq.), was coupled using coupling agents such as HBTU, COMU, DEPBT, and DIC, preferably DEPBT (2.0-4.0 eq.) and oxymapure HOBt, preferably oxymapure (2.0-4.0 eq.) and DIPEA NMM, TMP, preferably DIPEA (5.0-8.0 eq.) and $MgCl_2$, $ZnCl_2$, preferably $MgCl_2$ (0.01-0.1 eq) and DMF/NMP mixture as solvent. The reaction was performed nitrogen atmosphere and r.t. Upon completion of coupling of the amino acid confirmed by Kaiser Test, the excess reagents were drained and washed the peptidyl resin with 3×10 v DMF.

Stage-3: Synthesis of Fmoc-Gly$^{35}$-Arg(Pbf)$^{36}$-Gly$^{37}$-Wang Resin

Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Gly-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and $MgCl_2$, $ZnCl_2$, preferably $MgCl_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-4: Synthesis of Fmoc-Arg(Pbf)$^{34}$-Gly$^{35}$-Arg(Phf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Arg(Pbf)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and $MgCl_2$, $ZnCl_2$, preferably $MgCl_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-5: Synthesis of Fmoc-Val$^{33}$-Arg(Pbf)$^{34}$-Gly$^{35}$-Arg(Pbf)$^{36}$-Gly$^{37}$-Wang Resin v) Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Val-OH (2.0-4.0 eq.), was coupled using coupling agents such as HBTU, COMU, DEPBT, and DIC, preferably DEPBT (2.0-4.0 eq.) and oxymapure. HOBt, preferably oxymapure (2.0-4.0 eq.) and DIPEA, NMM, TMP, preferably DIPEA (5.0-8.0 eq.) and $MgCl_2$, $ZnCl_2$, preferably $MgCl_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-6: Synthesis of Fmoc-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Leu-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-7: Synthesis of Fmoc-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Trp(Boc)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-8: Synthesis of Fmoc-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Ala-OH (2.0-4.0 eq.) was coupled using coupling agents such as HBTU, COMU, DEPBT, and DIG, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-9: Synthesis of Fmoc-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Ile-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-10: Synthesis of Fmoc-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Phf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt DMF. The Fmoc-Phe-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_{12}$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-11 Synthesis of Fmoc-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin xi) Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Glu(O$^t$Bu)-OH (2.0-4.0 eq.), was coupled using coupling agents such as HBTU COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-12: Synthesis of Fmoc-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Lys(Mtt)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-13: Synthesis of Fmoc-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min, followed by the resin was washed with 3-5*8 v 0.01-0.1 M HOBt in DMF. The Fmoc-Ala-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-14 Synthesis of Fmoc-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried our by washing the resin using 15-25% piperidine in DMF two times for 5 and 10 min, followed by the resin was washed with 3-5*8 v 0.01-0.1 M HOBt in DMF. The Fmoc-Ala-OH (2.0-4.0 eq.), was coupled using coupling agents such as HBTU, COMU, DEPBT, and DIC, preferably DEPBT (2.0-4.0 eq.) and oxymapure, HOBt, preferably oxymapore (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-15: Synthesis of Fmoc-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25 piperidine in DMF two times for 5 and 10 min. followed by the resin was washed with 3-5*8 v 0.01-0.1 M HOBt in DMF. The Fmoc-Glu(Trt)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-16: Synthesis of Fmoc-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Gly-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-17: Synthesis of Fmoc-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Glu(O$^t$Bu)-OH (2.0-4.0 eq.), was coupled using coupling agents such as HBTU, COMU, DEPBT, and DIC, preferably DEPBT (2.0-1.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably. MgCl$_2$ (0.01-0.1 eq.) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-18: Synthesis of Fmoc-Leu$^{20}$-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min, followed by the resin was washed with 3-5*8 v 0.01-0.1 M HOBt in DMF. The Fmoc-Leu-OH (2.0-4.0 eq.), was coupled using coupling agents such as HBTU, COMU, DEPBT, and DIC preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-19: Synthesis of Fmoc-Tyr($^t$Bu)$^{19}$-Leu$^{20}$-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Tyr($^t$Bu)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-20: Synthesis of Fmoc-Ser($^t$Bu)$^{18}$-Tyr($^t$Bu)$^{19}$-Leu$^{20}$-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min, followed by the resin was washed with 3-5*8 v 0.01-0.1 M HOBt in DMF. The Fmoc-Ser($^t$Bu)-OH (2.0-4.0 eq.), was coupled using coupling agents such as HBTU, COMU, DEPBT, and DIC, preferably DEPBT (2.0-4.0 eq.) and oxymapure. HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq.) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-21: Synthesis of Fmoc-Ser($^t$Bu)$^{17}$-Ser($^t$Bu)$^{18}$-Tyr($^t$Bu)$^{19}$-Leu$^{20}$-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Ser($^t$Bu)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-22: Synthesis of Fmoc-Val$^{16}$-Ser($^t$Bu)$^{17}$-Ser($^t$Bu)$^{18}$-Tyr($^t$Bu)$^{19}$-Leu$^{20}$-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Val-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-23: Synthesis of Fmoc-Asp(O$^t$Bu)$^{15}$-Val$^{16}$-Ser($^t$Bu)$^{17}$-Ser($^t$Bu)$^{18}$-Tyr($^t$Bu)$^{19}$-Leu$^{20}$-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 mm, followed by the resin was washed with 3-5*8 v 0.01-0.1 M HOBt in DMF. The Fmoc-Asp(O$^t$Bu)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-24: Synthesis of Fmoc-Ser($^t$Bu)$^{14}$-Asp(O$^t$Bu)$^{15}$-Val$^{16}$-Ser($^t$Bu)$^{17}$-Ser($^t$Bu)$^{18}$-Tyr($^t$Bu)$^{19}$-Leu$^{20}$-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min, followed by the resin was washed with 3-5*8 v 0.01-0.1 M HOBt in DMF. The Fmoc-Ser($^t$Bu)-OH (2.0-4.0 eq.). was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-25: Synthesis of Fmoc-Thr($^t$Bu)$^{13}$-Ser($^t$Bu)$^{14}$-Asp(O$^t$Bu)$^{15}$-Val$^{16}$-Ser($^t$Bu)$^{17}$-Ser($^t$Bu)$^{18}$-Tyr($^t$Bu)$^{19}$-Leu$^{20}$-Glu($^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt, in DMF. The Fmoc-Thr($^t$Bu)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and at an elevated temperature around 30-45° C. Upon completion of coupling of the amino acid confirmed by Kaiser Test, the excess reagents were drained and washed the peptidyl resin with 3×10 v DMF.

Stage-26: Synthesis of Fmoc-Phe$^{12}$-Thr($^t$Bu)$^{13}$-Ser($^t$Bu)$^{14}$-Asp(O$^t$Bu)$^{15}$-Val$^{16}$-Ser($^t$Bu)$^{17}$-Ser($^t$Bu)$^{18}$-Tyr($^t$Bu)$^{19}$-Leu$^{20}$-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{32}$-Arg(Pbf)$^{34}$-Gly$^{35}$-Arg(Pbf)$^{36}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Phe-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably; DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and at an elevated temperature around 30-45° C. Upon completion of coupling of the amino acid confirmed by Kaiser Test, the excess reagents were drained and washed the peptidyl resin with 3×10 v DMF.

Stage-27: Synthesis of Fmoc-Thr($^t$Bu)$^{11}$-Phe$^{12}$-Thr($^t$Bu)$^{13}$-Ser($^t$Bu)$^{14}$-Asp(O$^t$Bu)$^{15}$-Val$^{16}$-Ser($^t$Bu)$^{17}$-Ser($^t$Bu)$^{18}$-Tyr($^t$Bu)$^{19}$-Leu$^{20}$-Glu(O$^t$Bu)$^{21}$-Gly$^{22}$-Glu(Trt)$^{23}$-Ala$^{24}$-Ala$^{25}$-Lys(Mtt)$^{26}$-Glu(O$^t$Bu)$^{27}$-Phe$^{28}$-Ile$^{29}$-Ala$^{30}$-Trp(Boc)$^{31}$-Leu$^{32}$-Val$^{33}$-Arg(Pbf)$^{34}$-Gly$^{35}$-Arg(Pbf)$^{35}$-Gly$^{37}$-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt DMF. The Fmoc-Thr($^t$Bu)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl$_2$, ZnCl$_2$, preferably MgCl$_2$ (0.01-0.1 eq) and DMF/NMP mixture as solvent. The reaction was performed in nitrogen atmosphere and at an elevated temperature around 30-45° C. Upon completion of coupling of the amino acid confirmed by Kaiser Test, the excess reagents were drained and washed the peptidyl resin, With 3×10 v DMF.

Stage-28: Synthesis of Fmoc-Gly$^{10}$-Thr($^t$Bu)$^{11}$-Phe$^{12}$-Thr($^t$Bu)$^{13}$-Ser($^t$Bu)$^{14}$-Asp(O$^t$Bu)$^{15}$-Val$^{16}$-Ser($^t$Bu)$^{17}$-Ser($^t$Bu)$^{18}$-Tyr($^t$Bu)$^{19}$-Leu$^{20}$-Glu (O$^t$Bu)$^{21}$-Gly$^{22}$-Glu(Trt)$^{23}$-Ala$^{24}$-

Ala²⁵-Lys(Mtt)²⁶-Glu(O^tBu)²⁷-Phe²⁸-Ile²⁹-Ala³⁰-Trp(Boc)³¹-Leu³²-Val³²-Arg(Pbf)³⁴-Gly³⁵-Arg(Pbf)³⁶-Gly³⁷-Wang Resin Fmoc-deprotection of the loaded amino acid was carried out by washing the resin using 15-25% piperidine it DMF two times for 5 and 10 min. followed by the resin was washed with 3-5*8 v 0.01-0.1 M HOBt in DMF. The Fmoc-Gly-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl₂, ZnCl₂, preferably MgCl₂ (0.01-0.1 eq) and DMF/NMP mixture as solvent. The reaction was performed in nitrogen atmosphere and at an elevated temperature around 30-45° C. Upon completion of coupling of the amino acid confirmed by Kaiser Test, the excess reagents were drained and washed the peptidyl resin with 3×10 v DMF.

Stage-29: Synthesis of Fmoc-Glu(O^tBu)⁹-Gly¹⁰-Thr(^tBu)¹¹-Phe¹²-Tbr(^tBu)¹³-Ser(^tBu)¹⁴-Asp(O^tBu)¹⁵-Val¹⁶-Ser(^tBu)¹⁷-Ser(^tBu)¹⁸-Tyr(^tBu)¹⁹-Leu²⁰-Glu(O^tBu)²¹-Gly²²-Glu(Trt)²³-Ala²⁴-Ala²⁵-Lys(Mtt)²⁶-Glu(O^tBu)²⁷-Phe²⁸-Ile²⁹-Ala³⁰-Trp(Boc)³¹-Leu³²-Val³³-Arg(Pbf)³⁴-Gly³⁵-Arg(Pbf)³⁶-Gly³⁷-Wang Resin Fmoc-deprotection of the loaded amino acid was carried out by washing the resin using 15-25% piperidine in DMF two times for 5 and 10 min. followed by the resin was washed with 3-5*8 v 0.01-0.1 M HOBt in DMF. The Fmoc-Glu(O^tBu)-OH (2.0-4.0 eq.), was coupled using coupling agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl₂, ZnCl₂, preferably MgCl₂ (0.01-0.1 eq.) and DMF/NMP mixture as solvent. The reaction was performed in nitrogen atmosphere at an elevated temperature around 30-45° C., Upon completion of coupling of the amino acid confirmed by Kaiser Test, the excess reagents were drained and washed the peptidyl resin with 3×10 v DMF.

Stage-30: Synthesis of Fmoc-Ala⁸-Glu(O^tBu)⁹-Gly¹⁰-Thr(^tBu)¹¹-Phe¹²-Thr(^tBu)¹³-Ser(^tBu)¹⁴-Asp(O^tBu)¹⁵-Val¹⁶-Ser(^tBu)¹⁷-Ser(^tBu)¹⁸-Tyr(^tBu)¹⁹-Leu²⁰-Glu(O^tBu)²¹-Gly²²-Glu(Trt)²³-Ala²⁴-Ala²⁵-Lys(Mtt)²⁶-Gly(O^tBu)²⁷-Phe²⁸-Ile²⁹-Ala³⁰-Trp(Boc)³¹-Leu³²-Val³³-Arg(Pbf)³⁴-Gly³⁵-Arg(Pbf)³⁶-Gly³⁷-Wang Resin Fmoc-deprotection of the loaded amino acid was carried out by washing the resin using 15-25% piperidine in DMF two times for 5 and 10 min, followed by the resin was washed with 3-5*8 v 0.01-0.1 M HOBt in DMF. The Fmoc-Ala-OH (2.0-4.0 eq.), was coupled using coupling, agents such as HBTU, COMU, DEPBT, and DIC, preferably DEPBT (2.0-4.0 eq.) and oxymapure, HOBt, preferably oxymapure (2.0-4.0 eq.) and DIPEA, NMM, TMP, preferably DIPEA (5.0-8.0 eq.) and MgCl₂, ZnCl₂, preferably MgCl₂, (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-31; Synthesis of Boc-His(Trt)⁷-Ala⁸-Glu(O^tBu)⁹-Gly¹⁰-Thr(^tBu)¹¹-Phe¹²-Thr(^tBu)¹³-Ser(^tBu)¹⁴-Asp(O^tBu)¹⁵-Val¹⁶-Ser(^tBu)¹⁷-Ser(^tBu)¹⁸-Tyr(^tBu)¹⁹-Leu²⁰-Glu(O^tBu)²¹-Gly²²-Glu(Trt)²³-Ala²⁴-Ala²⁵-Lys(Mtt)²⁶-Glu(O^tBu)²⁷-Phe²⁸-Ile²⁹-Ala³⁰-Trp(Boc)³¹-Leu³²-Val³³-Arg(Pbf)³⁴-Gly³⁵-Arg(Pbf)³⁶-Gly³⁷-Wang Resin Fmoc-deprotection of the loaded amino acid was carried out by washing the resin using 15-25 piperidine in DMF two times for 5 and 10 min, followed by the resin was washed with 3-5*8 v 0.01-0.1 M HOBt in DMF. The Boc-His(Trt)-OH (3.0-5.0 eq.), was coupled using coupling agents, such as HBTU, COMU, DEPBT, and DIC, preferably DEPBT (3.0-5.0 eq.) and oxymapure, HOBt, preferably oxymapure (3.0-50 eq.) and DIPEA, NMM, TMP, preferably DIPEA (6.0-10.0 eq.) and MgCl₂, ZnCl₂, preferably MgCl₂ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-32: Synthesis of Boc-His(Trt)⁷-Ala⁸-Glu(O^tBu)⁹-Gly¹⁰-Thr(^tBu)¹¹-Phe¹²-Thr(^tBu)¹³-Ser(^tBu)¹⁴-Asp(O^tBu)¹⁵-Val¹⁶-Ser(^tBu)¹⁷-Ser(^tBu)¹⁸-Tyr(^tBu)¹⁹-Leu²⁰-Glu(O^tBu)²¹-Gly²²-Glu(Trt)²³-Ala²⁴-Ala²⁵-Lys(Fmoc-Glu-O^tBu)²⁶-Glu(O^tBu)²⁷-Phe²⁸-Ile²⁹-Ala³⁰-Trp(Boc)³¹-Leu³²-Val³³-Arg(Pbf)³⁴-Gly³⁵-Arg(Phf)³⁶-Gly³⁷-Wang Resin Branching of the peptide was carried out by removing Mtt protecting group of Lys²⁶ side chain by treating with 0.5-2.0% TFA in MDC, 15-20 cycles×10 v. The peptidyl resin was washed with MDC 2×10 v, 2×10 v, 2×10 v DMF, and 5-10.0% DIPEA in DMF, The Fmoc-Glu-OtBu (2.0-5.0 eq.), was coupled using coupling agents such as HBTU, COMU, DEPBT, and DIC, preferably DEPBT (2.0-5.0 eq.) and oxymapure. HOBt, preferably oxymapure (2.0-5.0 eq.) and DIPEA, NMM, TMP, preferably DIPEA (5.0-10.0 eq.) and MgCl₂, ZnCl₂, preferably MgCl₂ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-33: Synthesis of Boc-His(Trt)⁷-Ala⁸-Glu(O^tBu)⁹-Gly¹⁰-Thr(^tBu)¹¹-Phe¹²-Thr(^tBu)¹³-Ser(^tBu)¹⁴-Asp(O^tBu)¹⁵-Val¹⁶-Ser(^tBu)¹⁷-Ser(^tBu)¹⁸-Tyr(^tBu)¹⁹-Leu²⁰-Glu(O^tBu)²¹-Gly²²-Glu(Trt)²³-Ala²⁴-Ala²⁵-Lys (Palmitoyl-Glu-O^tBu)²⁶-Glu(O^tBu)²⁷-Phe²⁸-Ile²⁹-Ala³⁰-Trp(Boc)³¹-Leu³²-Val³³-Arg(Pbf)³⁴-Gly³⁵-Arg(Pbf)³⁶-Gly³⁷-Wang Resin Fmoc-deprotection of the loaded amino acid was carried out by washing the resin using 10-25% piperidine in DMF two times for 5 and 10 min. followed by the resin was washed with 3-5*8 v 0.01-0.1 M HOBt in DMF. The hexadecanoic acid (2.0-5.0 eq.), was coupled using coupling agents such as HBTU, COMU, DEPBT, and DIC, preferably DIC (2.0-5.0 eq.) and oxymapure, HOBt, preferably oxymapure (2.0-4.0 eq.) and DIPEA, NMM, TMP, preferably DIPEA (5.0-8.0 eq.) and MgCl₂, preferably MgCl₂ (0.01-0.1 eq) and MDC as solvent. The reaction was performed in nitrogen atmosphere and r.t. Upon completion of coupling of the amino acid confirmed by Kaiser Test, the excess reagents were drained and washed the peptidyl resin with 3×10 v DMF.

Stage-34: Synthesis of H-His⁷-Ala⁸-Glu⁹-Gly¹⁰-Thr¹¹-Phe¹²-Thr¹³-Ser¹⁴-Asp¹⁵-Val¹⁶-Ser¹⁷-Ser¹⁸-Tyr¹⁹-Leu²⁰-Glu²¹-Gly²²-Glu²³-Ala²⁴-Ala²⁵-Lys(γ-Glu-palmitoyl)²⁶-Glu²⁷-Phe²⁸-Ile²⁹-Ala³⁰-Trp³¹-Leu³²-Val³³-Arg³⁴-Gly³⁵-Arg³⁶-Gly³⁷-OH The loaded peptidyl resin was washed with DMF 2×10 v, MDC 2×10 v, MeOH 2×10 v, and MTBE 3×10 v. The total cleavage of the peptide was carried out using TFA, phenol, TIS, H₂O Thioanisole cocktail mixture. The peptide—TFA cocktail was concentrated and added to chilled MTBE 5-15 v. The precipitated compound was isolated through centrifugation and/or filtration and dried in VTD and taken forward for purification (process yield 18.25%, purity 51.3%).

EXAMPLE 2

Synthesis of Liraglutide Using $CuCl_2$

The process is same as described in the example 1, and only the change is in place of $MgCl_2$, $CuCl_2$ is employed as catalyst during sequential coupling of all the individual amino acids (process yield 17.84%, purity 51.16%).

EXAMPLE 3

Synthesis of Liraglutide Using HFIP-TES-TFE Cocktail or Deprotection of Mtt Protecting Group The process is same as described in the example 1, and only the change is in Lys(Mtt)$^{26}$ removal wherein 5.0-40.0% HFIP, TES 2.0-10.0% TFE 5.0-10% in MDC 10-30 V was employed and mixture was agitated for 2-6 h (actual process yield 21.23%, purity 51.7%).

EXAMPLE 4

Synthesis of Liraglutide

The process is same as described in the example 1, and only the change is inorganic salts are not used during coupling (process yield 6.79%, purity 34.4%).

EXAMPLE 5

Synthesis of Liraglutide without Using Inorganic Salt

The process is same as described in the example 1, and only the change is inorganic salts are not used during coupling and IPA wash given in place 0.1 M HOBt in DMF (process yield 8.62%, purity 39.1%).

EXAMPLE 6

Synthesis of Liraglutide Using Coupling of Pal-Glu-OtBu Side Chain

Branching of the peptide was carried out by removing Mtt protecting group of Lys$^{26}$ side chain by treating with 0.5-2.0% TFA its MDC, 15-20 cycles×10 v. The peptidyl resin was washed with MDC 2×10 v, 2×10 v, 2×10 v DMF, and 5-10.0% DIPEA in DMF. The Pal-Glu-OtBu side chain (2.0-5.0 eq., represented in FIG. II), was coupled using coupling, agents such as HBTU, COMU, DEPBT, and DIC, preferably DEPBT (2.0-5.0 eq.) and oxymapure, HOBt, preferably oxymapure (2.0-5.0 eq.) and DIPEA. NMM, TMP, preferably DIPEA (5.0-10.0 eq.) and $MgCl_2$, $ZnCl_2$, preferably $MgCl_2$ (0.01-0.1 eq) and DMF/NMP mixture as solvent. The reaction was performed in nitrogen atmosphere and r.t. Upon completion of coupling of the amino acid confirmed by Kaiser Test, the excess reagents were drained and washed the peptidyl resin with 3×10 v DMF.

EXAMPLE 7

Synthesis of Liraglutide

The process is same as described in example 1, and the Mtt removal has been carried out as described in example 3. An additional, 0.01-0.1 M HOBt/DMF wash has been given after each Fmoc-deprotection step to ensure complete removal of piperidine as well as avoid aggregation of linear peptide during synthesis (actual process yield 27.0%, purity >60.0%).

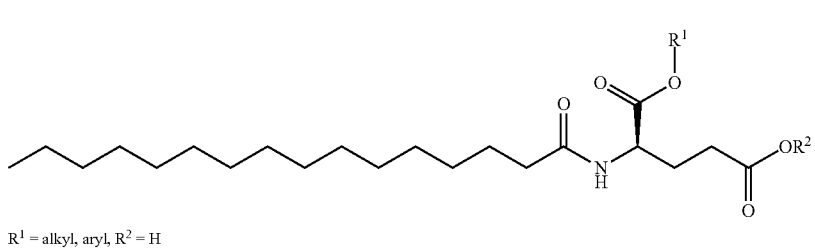

FIG. II $R^1$ = alkyl, aryl, $R^2$ = H

EXAMPLE 8

Purification of Liraglutide

Crude liraglutide was dissolved in dilute ammonium carbonate solution containing 5-40% ACN at a concentration of 5-75 mg/ml and was loaded onto pre-equilibrated 100-10-C8 column (10 mm×250 mm). This was followed by 0.2 CV of the diluent. The bound liraglutide was elated using a step gradient of the mobile phase (A: 0.1% TEA in water; B: 0.1% TEA in ACN: IPA). Fractions having purity >92% was concentrated under vacuum followed 1 iso-electric point precipitation. The precipitate was recovered by centrifugation. The recovered precipitate was again subjected to another RP-HPLC step on the column 100-10-C8 column (10 mm×250 mm). The bound liraglutide was eluted using gradient elution of the mobile phase composed of viz. A: dilute ammonium acetate; B: ACN. Fractions >98.5% were pooled, concentrated under vacuum, precipitated at iso-electric point & finally lyophilized.

EXAMPLE 9

Purification of Liraglutide

Crude liraglutide was dissolved in dilute ammonia solution at a concentration of 10-75 mg/ml and was subjected to RP-HPLC-1 step on a 100-10-C8 column (10 mm×250 mm). This was followed by 0.2 CV of the diluent. The bound liraglutide was eluted using a step gradient of the mobile phase (A: 0.1% TFA in water; B: 0.1% TFA in ACN: IPA). Fractions having purity >90% was concentrated under vacuum followed by iso-electric point precipitation. The precipitate was recovered by centrifugation. The recovered precipitate was again subjected to a RP-HPLC-2 step on the column 100-10-C8 column (10 mm×250 mm). The bound liraglutide was eluted using gradient elution of the mobile phase composed of viz. A: TFA in water; B: TFA in Methanol. This step helped in reduction of a specific impurity. Fractions >93% were pooled, diluted with ammonium acetate and loaded onto RP-HPLC-3 step on the column 100-10-C8 column (10×250 mm). The bound liraglutide was elated using gradient elution of the mobile phase composed of viz. A: Ammonium acetate; B: ACN. Fractions >98.5% were pooled, concentrated vacuum, precipitated at iso-electric point & finally lyophilized.

The invention claimed is:

1. A process for the preparation of liraglutide comprising the steps of,
   a) loading of C-terminal glycine to a resin solid-phase support in the presence of a coupling agent;
   b) capping of the unreacted functional sites;
   c) sequential coupling of $N^\alpha$- and side chain protected amino acids to prepare the backbone of liraglutide, in the presence of a coupling agent and an inorganic salt;
   d) deprotecting the side chain protecting group of lysine;
   e) coupling of glutamic acid and palmitic acid to the side chain of lysine in the presence of a coupling agent and an inorganic salt; and
   f) obtaining crude liraglutide by removal of protective groups and cleavage of peptide from the resin,
   wherein the process comprises coupling of amino acids 9 to 13 at a temperature range of 30-45° C.,
   wherein the inorganic salt is present in a catalytic amount and is selected from the group consisting of magnesium chloride, zinc chloride and copper chloride,
   wherein step (c) comprises deprotection of the Fmoc group of each loaded amino acid using piperidine in DMF or a piperidine/DBU/DMF mixture, wherein after each Fmoc deprotection step there is a washing step using HOBt in DMF and deprotection of the methyltrityl protecting group of lysine.

2. A process for the preparation of liraglutide comprising the steps of,
   a) coupling of $N^\alpha$-Fmoc-protected glycine (Fmoc-Gly-OH) to a resin solid-phase support in the presence of a coupling agent;
   b) sequential coupling of $N^\alpha$- and side chain protected amino acids to prepare backbone of liraglutide, in the presence of a coupling agent and an inorganic salt;
   c) deprotecting of the side chain protecting group of lysine;
   d) coupling of palmitoyl-glutamic acid (Pal-Glu-O$^t$Bu) side chain to the side chain of lysine in the presence of a coupling agent and an inorganic salt; and
   e) obtaining crude liraglutide by removal of protective groups and cleavage of peptide from the resin,
   wherein, the process comprises coupling of amino acids 9 to 13 at a temperature range of 30-45° C.,
   wherein the inorganic salt is present in a catalytic amount and is selected from the group consisting of magnesium chloride, zinc chloride and copper chloride,
   wherein step (c) comprises deprotection of the Fmoc group of each loaded amino acid using piperidine in DMF or a piperidine/DBU/DMF mixture, wherein after each Fmoc deprotection step there is a washing step using HOBt in DMF and deprotection of the methyltrityl protecting group of lysine.

3. The process of claim 1 which involves coupling agents selected from the group consisting of HBTU, COMU, DEPBT, DIC, and any combination thereof.

4. The process of claim 1 which involves coupling additives selected from the group consisting of oxymapure, HOBt, and any combination thereof.

5. The process of claim 1, wherein coupling of Boc-Histidine uses a coupling agent mixture selected from the group consisting of HBTU-oxyma pure, COMU-oxyma pure, DEPBT-oxyma pure, and DIC-oxyma pure.

6. The process of claim 5, wherein the coupling of Boc-Histidine uses DEPBT-oxyma pure.

7. The process of claim 1 comprising, deprotection of a Methyltrityl protecting group of lysine using HFIP/TES/TFE/MDC.

8. The process of claim 1, further comprising purifying crude liraglutide.

9. The process of claim 1, wherein capping of the unreacted functional sites is carried out using acetic anhydride and organic base, and coupling of glutamic acid and palmitic acid to the side chain of lysine is carried out in a sequential manner.

10. The process of claim 2, further comprising purifying crude liraglutide.

11. The process of claim 2, wherein deprotection of the side chain protecting group of lysine comprises deprotection of the side chain methyltrityl protecting group of lysine using TFA in dichloromethane, and subsequent coupling of palmitoyl-glutamic acid (Pal-Glu-OtBu) side chain to the deprotected side chain of lysine in the presence of a coupling agent selected from HBTU, COMU, DEPBT, and DIC and an additive selected from oxymapure and HOBt, or a combination of coupling agents/additives thereof, and an inorganic salt.

12. The process of claim 2, wherein deprotection of the methyltrityl protecting group of lysine comprises using HFIP/TES/TFE/MDC, and/or wherein coupling of protected glutamic acid and palmitic acid is carried out in sequential manner to the side chain of lysine in the presence of coupling agent and an inorganic salt.

13. The process of claim 1, wherein the catalytic amount ranges from 0.01 to 0.1 eq.

14. The process of claim 2, wherein the catalytic amount ranges from 0.01 to 0.1 eq.

* * * * *